(12) United States Patent
Fischer et al.

(10) Patent No.: US 7,955,314 B2
(45) Date of Patent: Jun. 7, 2011

(54) ARTICULATING HANDLE FOR A DEFLECTABLE CATHETER AND METHOD THEREFOR

(75) Inventors: Brian Fischer, Minneapolis, MN (US); Brian Honebrink, Stillwater, MN (US)

(73) Assignee: Greatbatch Ltd., Clarence, NY (US)

( * ) Notice: Subject to any disclaimer, the term of this patent is extended or adjusted under 35 U.S.C. 154(b) by 1470 days.

(21) Appl. No.: 11/127,818

(22) Filed: May 12, 2005

(65) Prior Publication Data

US 2006/0258979 A1 Nov. 16, 2006

(51) Int. Cl.
*A61M 25/00* (2006.01)

(52) U.S. Cl. ........................................................ 604/528

(58) Field of Classification Search .................. 604/528, 604/95.01, 95.04, 95.05
See application file for complete search history.

(56) References Cited

U.S. PATENT DOCUMENTS

| | | | |
|---|---|---|---|
| 3,452,740 A | 7/1969 | Muller | |
| 4,178,920 A | 12/1979 | Cawood, Jr. et al. | |
| 4,898,577 A | 2/1990 | Bafger et al. | |
| 5,273,535 A * | 12/1993 | Edwards et al. | 604/95.01 |
| 5,472,017 A | 12/1995 | Kovalcheck | |
| 5,562,619 A | 10/1996 | Mirarchi et al. | |
| 5,601,658 A | 2/1997 | Chevillon et al. | |
| 5,861,024 A * | 1/1999 | Rashidi | 607/122 |
| 5,944,727 A | 8/1999 | Ahari et al. | |
| 6,171,277 B1 | 1/2001 | Ponzi et al. | |
| 6,579,278 B1 | 6/2003 | Bencini | |
| 7,524,301 B2 * | 4/2009 | Dubois et al. | 604/95.04 |
| 2003/0109778 A1 | 6/2003 | Rashidi | |

FOREIGN PATENT DOCUMENTS

| | | |
|---|---|---|
| EP | 0938871 A2 | 9/1999 |
| WO | WO-94/26347 A1 | 11/1994 |
| WO | WO-01/85246 A1 | 11/2001 |
| WO | WO-02/089891 A2 | 11/2002 |
| WO | WO-2006/124586 A2 | 11/2006 |
| WO | WO-2006/124586 A3 | 11/2006 |

* cited by examiner

*Primary Examiner* — Kevin C Sirmons
*Assistant Examiner* — Deanna K Hall
(74) *Attorney, Agent, or Firm* — Schwegman, Lundberg & Woessner, P.A.

(57) ABSTRACT

A catheter assembly includes a handle assembly, and a catheter body coupled with the handle assembly, where the catheter body extends to a deflectable distal end portion, and the deflectable distal end is controllable by a flexible element. A lever actuator member is operatively coupled with the flexible element, and movement of the actuator member provides for movement of the flexible element.

31 Claims, 12 Drawing Sheets

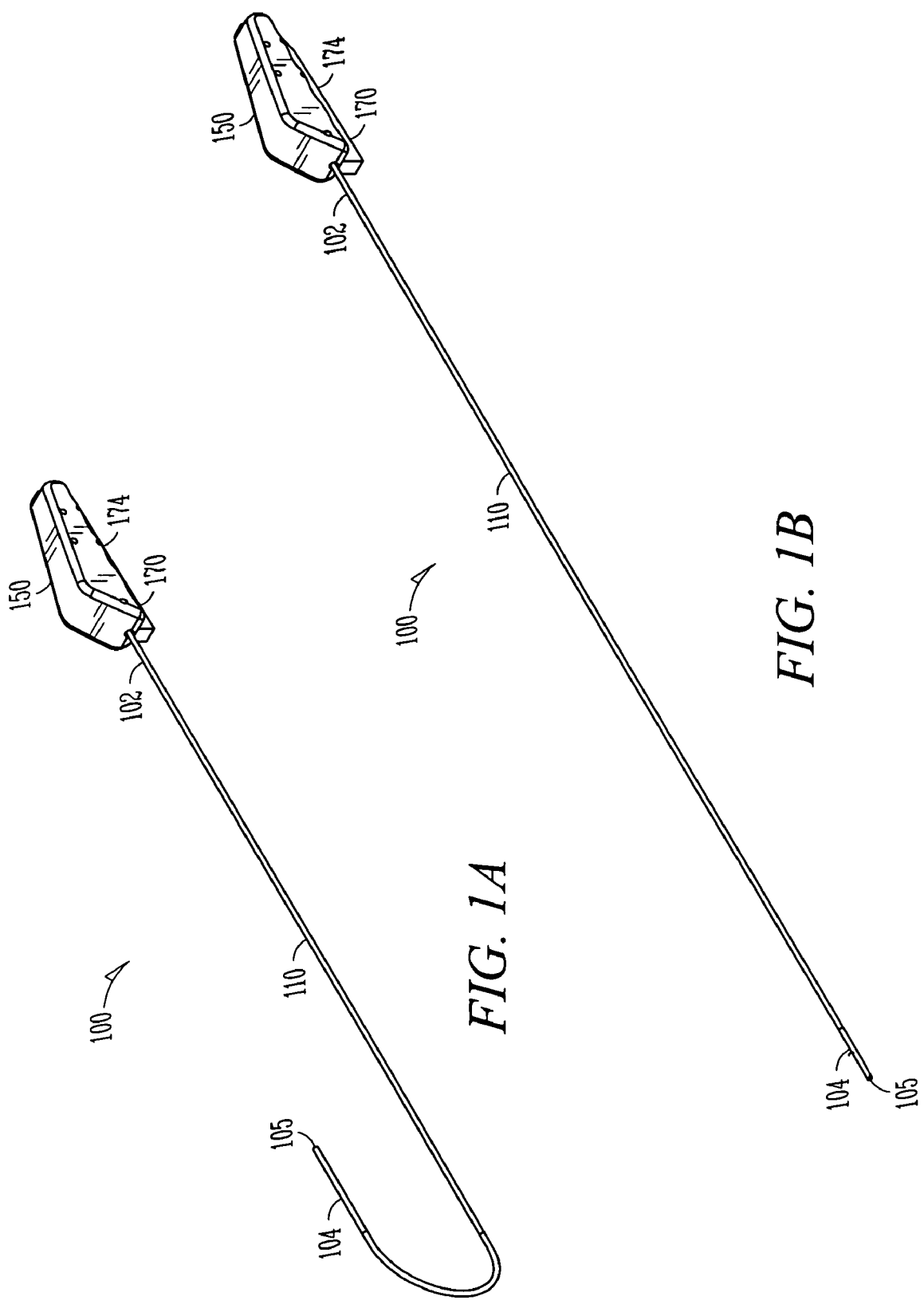

ARTICULATING HANDLE FOR A DEFLECTABLE CATHETER AND METHOD THEREFOR

TECHNICAL FIELD

The present document relates generally to deflectable catheter assemblies. More particularly, it pertains to an articulating handle assembly for a deflectable catheter.

BACKGROUND

Increase in the use of stents, leads, and ablation techniques in branch vessels has provided an increased demand in the placement techniques for the devices. For some procedures, it is necessary to initially position a guidewire into a desired part of the lumen of a desired vessel or duct, such as a blood vessel. After the guidewire is positioned within the desired location, a catheter or other tubular device may be positioned over the guidewire and used to convey other medical instruments into the desired blood vessel or duct.

Alternatively, a guiding catheter is used to negotiate the vasculature of a patient. One example of a guiding catheter is described in U.S. Pat. No. 4,898,577 to Badger et al. The Badger guiding catheter includes a single elongate shaft that has a deflectable distal portion controllable by a pull wire. Once the distal portion is at the required deflection or location within the patient, the medical instrument is fed through the catheter.

The deflectable catheter is controlled at a proximal end of the catheter by a control handle that operates the pull wire to deflect the catheter, for example, as shown in U.S. Pat. No. 6,171,277. However, with conventional catheter steering mechanisms, it is sometimes difficult to accurately position the catheters in certain body vessels, such as branch veins. For instance, the mechanisms are awkward or require the use of two hands. Other steering mechanisms require pull wires to be wound and unwound around a rotatable cam wheel, causing increased fatigue on the pull wires, and potentially shortening the life of the device. Furthermore, some deflectable catheters involve relatively large catheter sheaths. The larger sheaths can be difficult to manipulate within a patient, particularly when using a relatively small wheel mechanism or the above-discussed handle assemblies.

What is needed is a deflectable catheter that overcomes the shortcomings of previous deflectable catheters. What is further needed is a deflectable catheter that allows for more ease positioning of the distal end of the deflectable catheter, and that is usable with a single hand.

SUMMARY

A catheter assembly includes a handle assembly, and a catheter body coupled with the handle assembly, where the catheter body extends to a deflectable distal end portion, and the deflectable distal end portion is controllable by a flexible element. The catheter assembly further includes a lever actuator member operatively coupled with the flexible element, where the lever actuator member has a first lever position and a second lever position, and movement of the lever actuator member provides for movement of the flexible element and the deflectable distal end portion. The lever actuator has several options. For example, the lever actuator member can be disposed along a first surface of the handle assembly, where the lever actuator member is deflectable toward a second surface when moving from the first position to the second position, where the first surface is opposite the second surface. In another option, the lever actuator member is movable within a first plane, and the deflectable distal end portion is movable within a second plane, and the first plane is substantially non-parallel with the second plane. Several other options are further discussed below.

A method includes manipulating a catheter assembly, the catheter assembly including a handle assembly, a catheter body coupled with the handle assembly, the catheter body extending to a deflectable distal end portion, the deflectable distal end portion controllable by a flexible element and a lever actuator member mechanically associated with the flexible element, and movement of the lever actuator member provides for movement of the flexible element. The method further includes moving the lever actuator member from a first actuator position to a second actuator position including moving the lever actuator member from a position along a first surface of the handle assembly toward a second opposite surface of the handle assembly, moving the lever actuator member from the first actuator position deflects the distal end portion of the catheter body.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1A illustrates a perspective view of a catheter assembly as constructed in accordance with at least one embodiment.

FIG. 1B illustrates a perspective view of a catheter assembly as constructed in accordance with at least one embodiment.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

A deflectable catheter assembly is disclosed herein and includes a handle assembly, and a catheter body coupled with the handle assembly, where the catheter body extends to a deflectable distal end portion, and the deflectable distal end portion is controllable by a flexible element. The catheter assembly further includes a lever actuator member operatively coupled with the flexible element, where the lever actuator member has a first lever position and a second lever position, and movement of the lever actuator member provides for movement of the flexible element and the deflectable distal end portion. The catheter assembly will be described in more detail along with the illustrations.

Figure 1C:
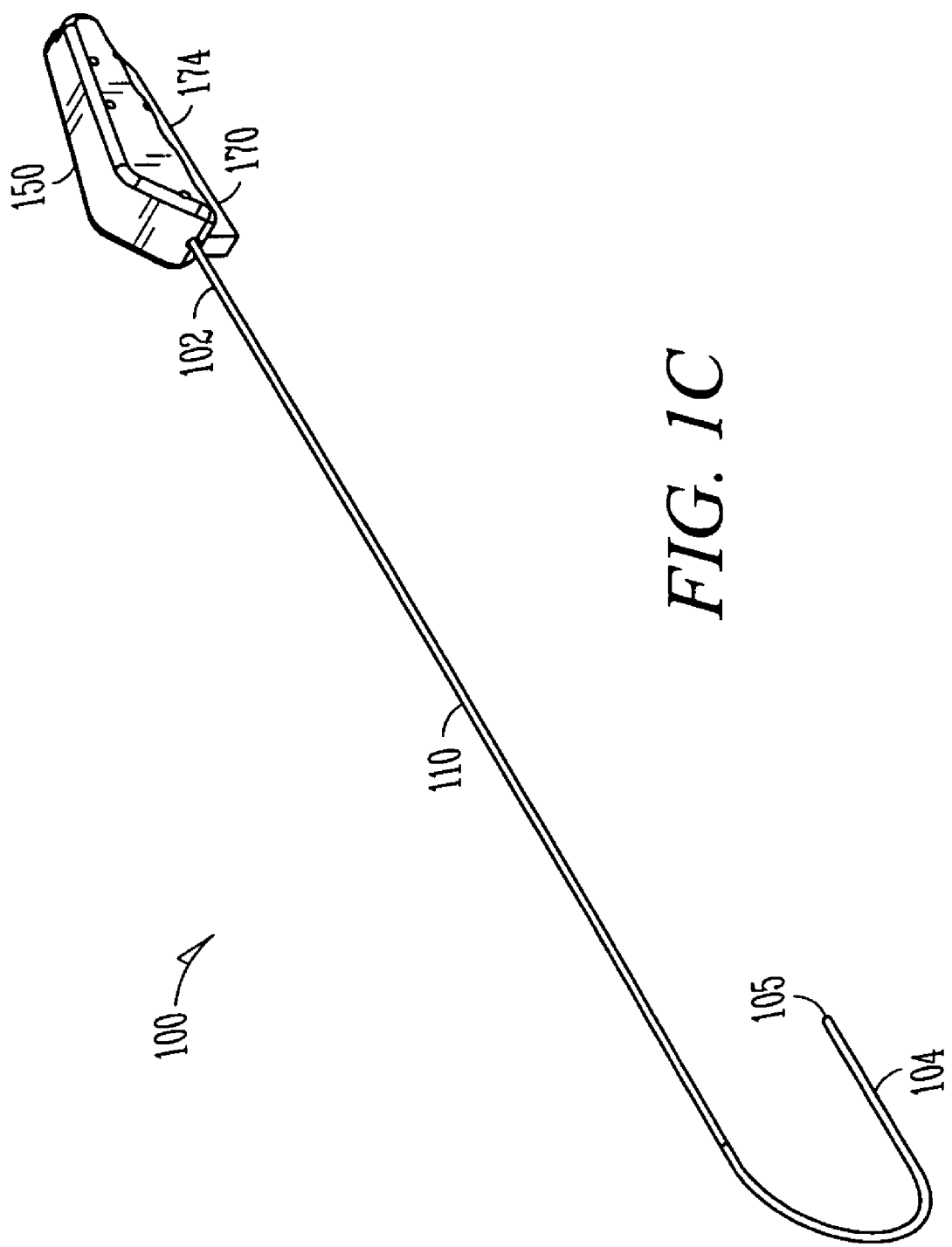
FIG. 1C illustrates a perspective view of a catheter assembly as constructed in accordance with at least one embodiment.
Figure 7A:
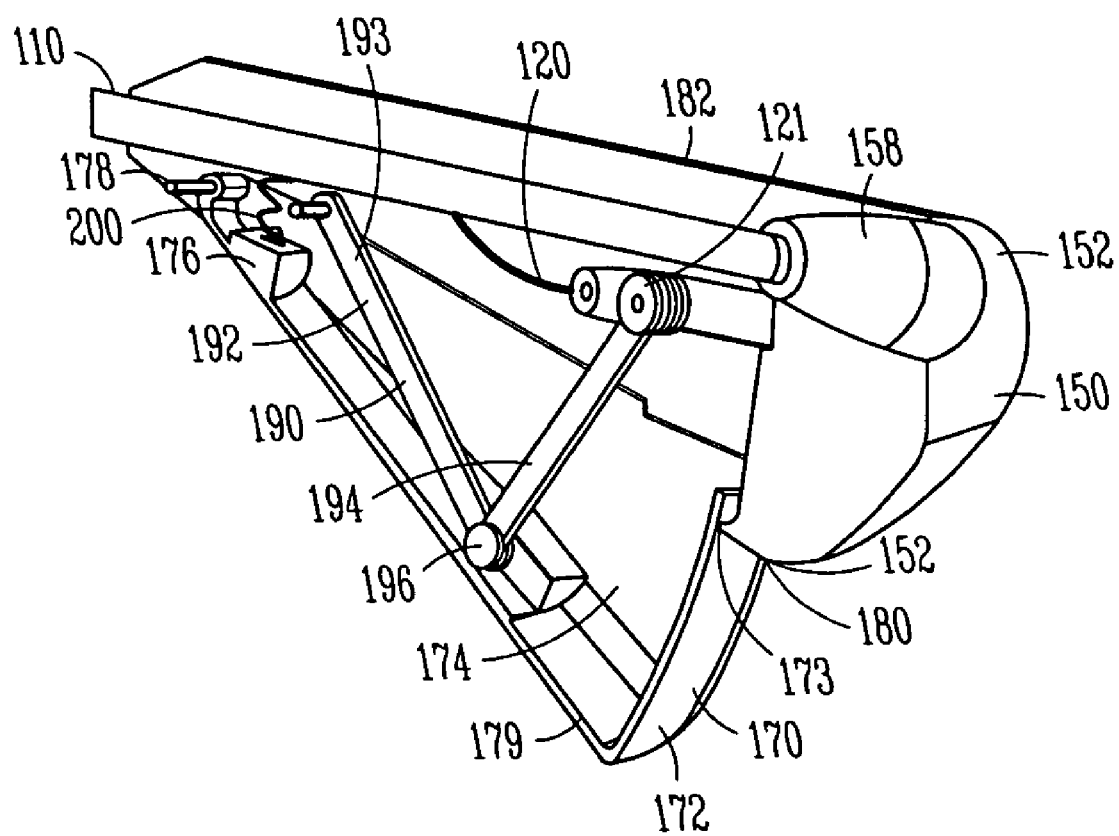
FIG. 7A illustrates a perspective view of a portion of catheter assembly as constructed in accordance with at least one embodiment.

FIGS. 1A, 1B, and 1C illustrate a deflectable catheter assembly 100, where FIGS. 1A and 1C illustrate the deflectable catheter assembly 100 in an articulated position, and FIG. 1B illustrates the deflectable catheter assembly 100 in an unarticulated position. The deflectable catheter assembly 100 includes a deflectable catheter body 110 and a handle assembly 150 that houses steering mechanisms for deflection of the catheter body 110. The handle assembly 150, as described in greater detail below, allows for the deflection of a distal end of the catheter body 110. In one option, the pull wire 120 (FIG. 7A) is operably connected to a lever actuator assembly that is, for example, rotated about a fulcrum to apply tension to the pull wire 120 (FIG. 7A). As tension is applied to the pull wire 120 (FIG. 7A), the pull wire anchor at the distal end of the catheter body 110 is pulled which causes the distal portion of the catheter body 110 to curve in a predetermined direction or directions.

The catheter body 110 comprises, in one option, an elongate tubular construction that is flexible yet substantially non-compressible along its length. The deflectable catheter body 110 extends from a proximal end portion 102 to a distal end portion 104, where the distal end portion 104 is disposed within a patient. At the distal end 104 is a distal tip 105. At the proximal end 102, the physician controls the deflection of the deflectable catheter body 110 with the handle assembly 150 and a pull wire 120 (FIG. 7A), as further described below. The distal end 104 is deflected to traverse various branch vessels with the catheter assembly 100.

The catheter body 110 includes a pull wire anchor that is secured to, for example, a distal portion of the catheter body 110. The pull wire 120 is mechanically secured to the pull wire anchor, for example, by welding the pull wire 120 to the pull wire anchor. It should be noted that the pull wire can be secured to the distal end 104 of the catheter body 110 in other manners. In one option, the catheter body 110 includes a stiffening member embedded therein, such as a braided stainless steel member. The stiffening member facilitates rotation of the distal end 104 from the proximal end 102, and also assists in preventing the catheter body 110 from collapsing.

The deflectable catheter body 110 includes a deflectable end portion 104 that is deflectable, for example, from a first position, as illustrated in FIG. 1A, to a second position, as illustrated in FIG. 1B. In another option, the second position can be as illustrated in FIG. 1C. In at least one option, the deflection of the catheter body 110 occurs within a first plane. However, it should be noted that the entire device can be rotated within the patient during use, for example, while deflecting the distal end, to access the varying and tortuous vasculature.

Several examples of the handle assembly 150 are shown in FIGS. 2-8. The handle assembly 150 extends from a handle distal end to a handle proximal end, and includes a handle assembly longitudinal axis. The handle assembly 150 includes a handle housing 152 that is designed to easily and comfortably fit into a practitioners hand, and to be easily manipulated with single handed use. In one option, the handle housing 152 are formed of a first portion and a second portion that are coupled together, for example, by one or more threaded fasteners. Other devices and/or methods for coupling the first and second portions of the handle housing 152 are suitable as well, such as, but not limited to, adhesive, welding, snap-fit, etc.

The handle housing 152 includes a handle lumen 158 therein. The handle lumen 158 is co-operatively aligned or connected with the delivery lumen of the catheter body 110 (FIG. 7A), and the handle lumen 158 (FIG. 7A) extends from a first end to a second end of the housing. The first end of the handle lumen 158, in one option, is disposed proximal to the distal end of the housing, and the second end of the handle lumen 158, is optionally disposed at the second end of the housing.

The housing 152 and delivery lumen are adapted to receive a medical instrument, such as, but not limited to, a guidewire, a lead, an ablating device, etc., through the second end of the housing 152. In one option, a valve 130 (FIG. 8) is coupled with the delivery lumen of the catheter body 110 (FIG. 7A). The valve 130 provides further prevention of inadvertent fluid leakage from the delivery lumen. In another option, a fitting such as a luer fitting is provided on or near the housing 152. In yet another option, a side port 132 is coupled with the valve 130, which allows for the valve 130 to be flushed with fluids. The side port 132 is disposed through a portion of the handle assembly 150, for example, through an opening 134, allowing access to the side port 132 by a physician or medical technician. It should be noted that the valve 130, the luer fitting, and/or the side port 132 can be combined with any of the above or below discussed embodiments.

The handle assembly 150 includes therein the actuator assembly 170 that is operatively coupled with and moves the pull wire 120 (FIG. 7A). Referring to FIG. 7A, the actuator assembly 170 includes an actuator 172 disposed through a slot 173 in a first surface 180 of the handle housing 152. The actuator 172 is manipulatable by an operator from at least a first position to a second position to deflect the distal end 104. In one option, the actuator 172 includes a lever member 174 that is easily manipulated by a single hand using a squeezing motion. The squeezing input from the hand is transferred into linear movement to provide the linear stroke for the pull wire on the proximal end, as further described below.

The lever actuator member 174 extends from a first member end 176 (FIG. 7A) to a second member end 179 (FIG. 7A), and in one option, is operatively coupled with the handle assembly 150 at a fulcrum 178 (FIG. 7A) or hinge, for example, although not limited to, a lower surface of the housing 152. The lever actuator member 174, in at least one option, moves about the fulcrum 178, for example, by a hinge, pivoting, or rotating movement. As the lever actuator member 174 moves about the fulcrum 178, the lever actuator member 174 moves toward a second opposite surface 182 of the handle housing 152, for example, in to and out of the slot 173 of the housing 152. In another option, the lever actuator member 174 is substantially aligned with a longitudinal axis of the handle housing 152 and rotates along the longitudinal axis, for example, parallel with the housing longitudinal axis.

The lever actuator member 174 is designed to be used by a single handed operation. For example, the user can squeeze the lever actuator member 174 and manipulate the distal end 104 of the catheter assembly. The lever actuator member 174 is resiliently coupled within the handle assembly such that squeezing the lever actuator member 174 deflects the distal end 104, for example, in a first direction, and releasing the lever actuator member 174 allows for the resilient member, discussed further below, to actuate or deflect the distal end 104 in a second direction. Further options which facilitate single-handed operation include the relative proportions of the lever actuator member 174. For example, the lever extends along the housing where the lever member 174 has a length greater than at least half a length of the handle length.

Figure 2:
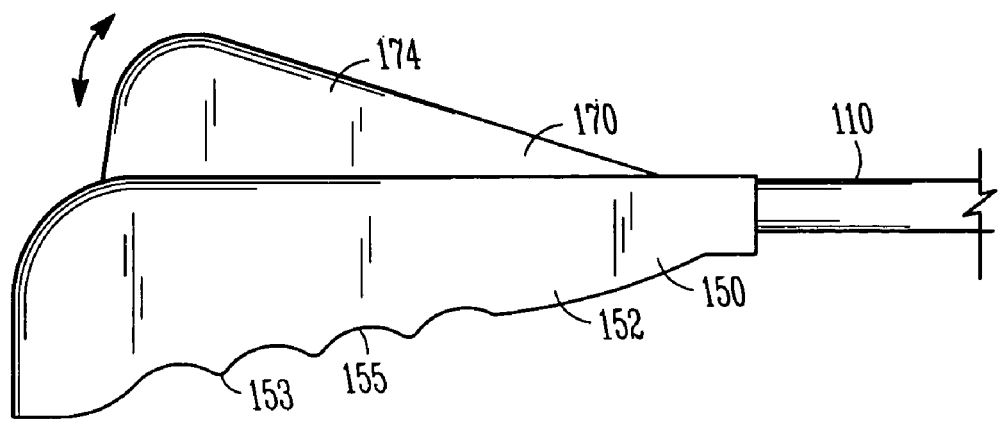
FIG. 2 illustrates a side elevational view of a catheter assembly as constructed in accordance with at least one embodiment.
Figure 3:
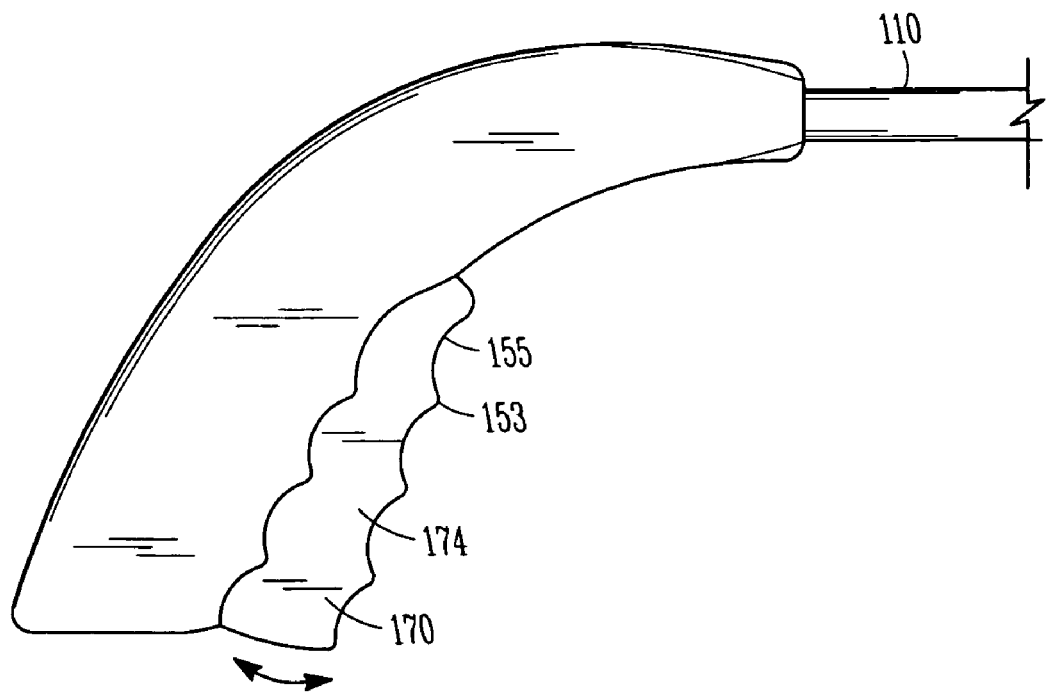
FIG. 3 illustrates a side elevational view of a catheter assembly as constructed in accordance with at least one embodiment.
Figure 4:
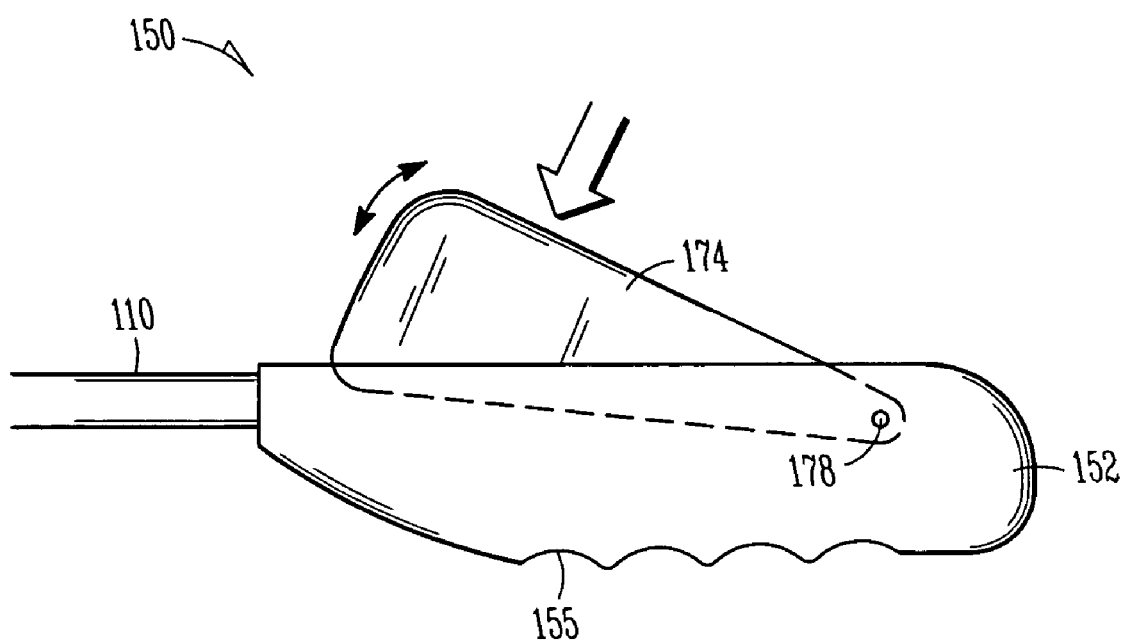
FIG. 4 illustrates a side elevational view of a catheter assembly as constructed in accordance with at least one embodiment.

Further options are illustrated in FIGS. 2-8. FIG. 2 illustrates a lever actuator member 174 disposed along an upper surface of the housing 152 and an optional grip portion 153 opposite from the lever actuator member 174. The grip portion 153 optionally includes recesses 155 to receive a user's fingers therein. In another option, as illustrated in FIG. 3, the handle housing 152 has a pistol-grip portion 153. In yet another option, which can be incorporated with any embodiment, the lever actuator member 174 includes a grip portion 153 with recesses 155 therein. FIG. 4 illustrates another option where the fulcrum 178 is disposed near the proximal end of the handle housing, and the lever actuator member 174 moves in and out of an upper surface of the handle housing. Opposite the member 174 is the grip portion 153 disposed along the lower portion of handle housing 152.

Figure 5:
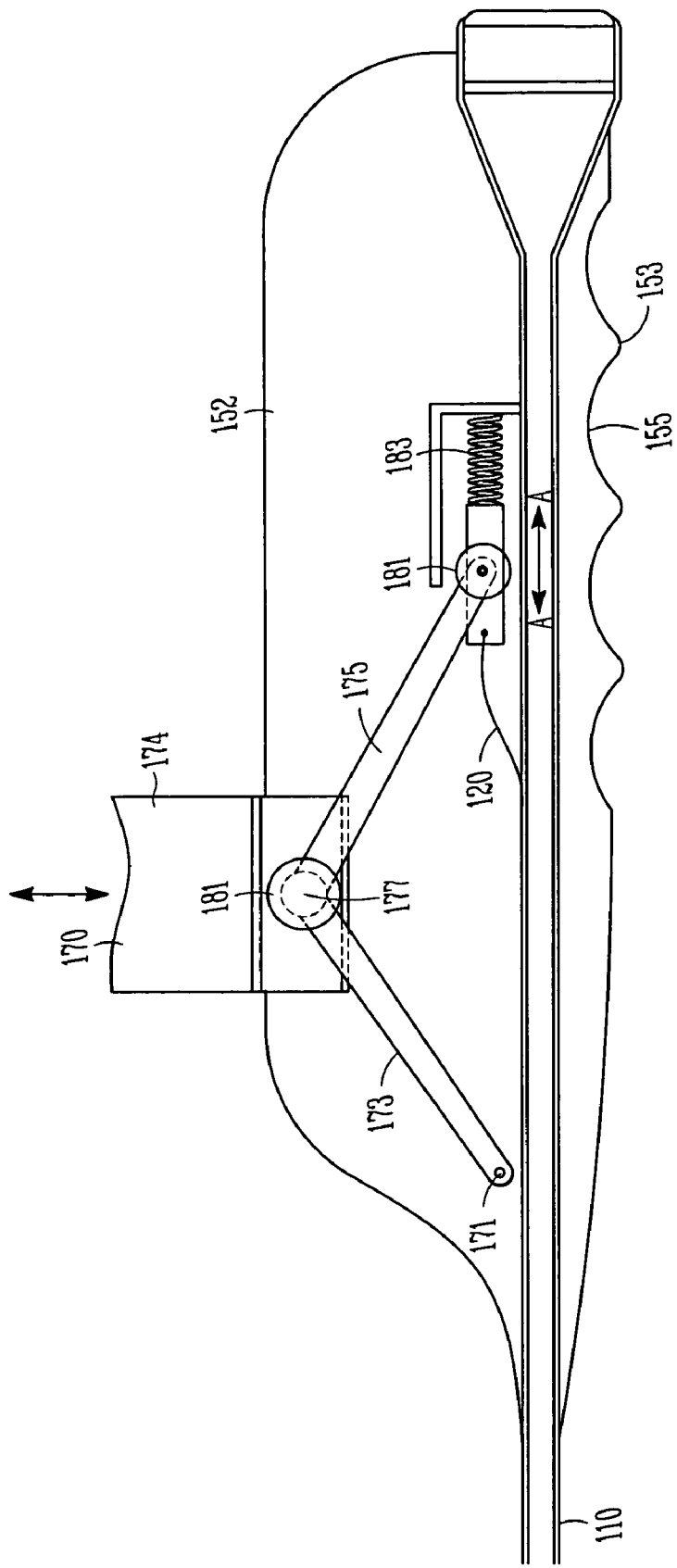
FIG. 5 illustrates a side elevational view of a catheter assembly as constructed in accordance with at least one embodiment.
Figure 6:
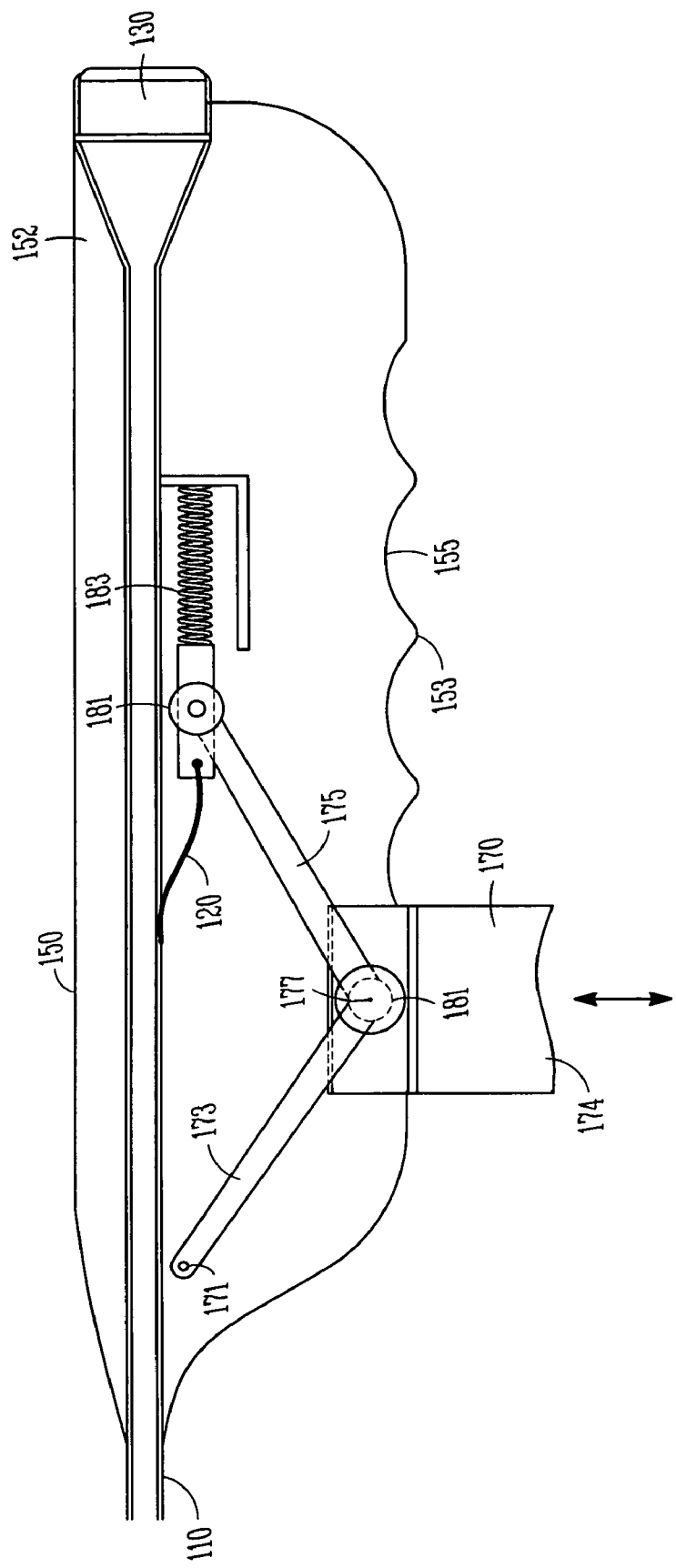
FIG. 6 illustrates a side elevational view of a catheter assembly as constructed in accordance with at least one embodiment.

FIGS. 5 and 6 illustrate additional options for the handle assembly 150. For example, FIG. 5 illustrates a handle assembly 150 with an actuator member 174 that is moved toward a location within the housing to actuate the assembly. Linkages 173, 175 are rotatably coupled with the actuator member 174, allowing for the pullwire to be pulled, and a distal end of the catheter body to be deflected. For instance, a first linkage 173 rotates about 171, and is hingedly coupled with the actuator member 174 at 177, for example with a roller 181. The second linkage 175 moves with the pull wire 120 along A-A, and is coupled with both the pull wire 120 and the actuator 174, for instance with one or more rollers 181. Optionally a spring 183, such as a compression spring, is disposed within the housing and assists in returning the pull wire 120 to a predetermined position, such as a J shape, or a straight position. As the actuator 174 is moved, the overall linkage length extends and retracts, which moves the pullwire 120 relative to the sheath, or catheter body. FIG. 6 illustrates another configuration for the handle assembly, with similar internal options as discussed above for FIG. 5. It should be noted that for both FIG. 5 and FIG. 6 many other embodiments discussed above and below and be incorporated therewith.

Figure 7B:
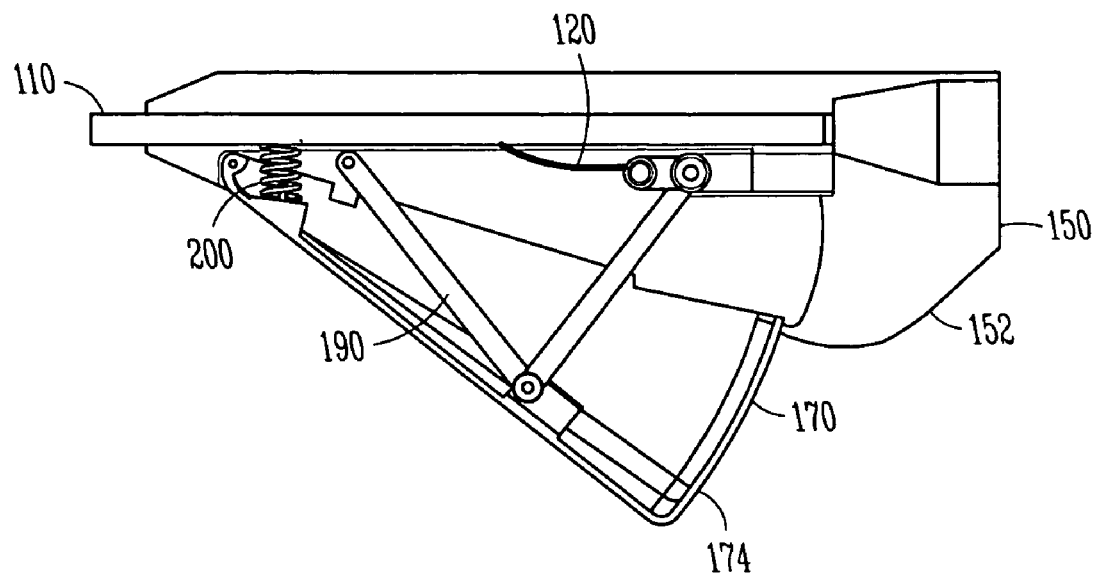
FIG. 7B illustrates a side elevational view of a portion of a catheter assembly as constructed in accordance with at least one embodiment.
Figure 7C:
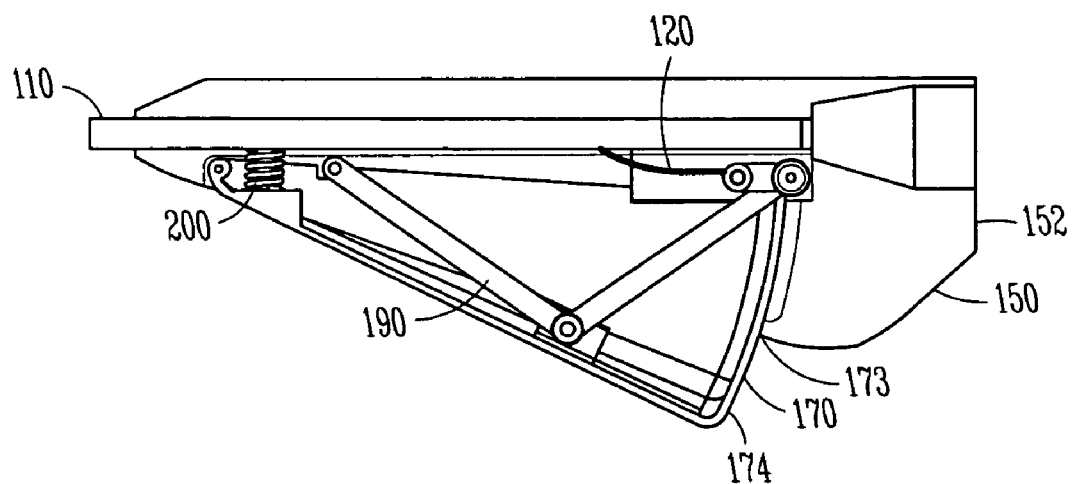
FIG. 7C illustrates a side elevational view of a portion of a catheter assembly as constructed in accordance with at least one embodiment.

The handle assembly 150 further includes an internal mechanism for translating the movement of the actuator member 174 to movement of the flexible element, such as, but not limited to, pull wire 120, resulting in deflection of the distal end of the catheter assembly. FIGS. 7A-7C illustrate one example. A resilient member 200, such as a spring, is operably disposed between a lever actuator member 174 and another element, such as the housing 152. The resilient member 200 allows for the lever actuator member 174 to return to a first position. A linkage 190 is disposed within the housing handle 152 and is operatively coupled with the housing 152 and the lever actuator member 174.

The linkage 190 includes a distal link 192, a proximal link 194, a lever member roller 196, and a handle roller 198. The distal link 192 is rotatably coupled with the housing 152 at a first end 193 and is rotatably coupled with the member roller 196 at a second end 195. The proximal link 194 is coupled with the member roller 196 at a first end 191 and with a pull wire assembly 121 at a second end 189. The pull wire assembly 121 moves within a portion of the housing 152 as the lever member actuates the linkage 190. The pull wire assembly 121 is mechanically fixed with the pull wire 120, such that as the pull wire assembly 121 is moved, the pull wire 120 is moved.

FIGS. 7B and 7C illustrate one example of the movement of the internal mechanism that allows for use of the catheter assembly. The lever actuator member 174 is moved from a first position (FIG. 7B) to a second position (FIG. 7C), for example, by a user squeezing the lever actuator member 174, and moves the linkages as illustrated in the figures. The linkages 190 move the pull wire assembly 121, and moves the pull wire 120. As the pull wire 120 is moved, this pulls on the pull wire anchor, and the distal end of the catheter body is deflected into position as desired by the physician. In at least one option, as the lever actuator is moved, for example within a first plane of movement, the distal end of the catheter body moves within a second plane of movement. Optionally, the first plane is substantially non-parallel with the second plane. In one option, an indicator is associated with the movement or deflection of the catheter body, such that feedback is provided while the body is being moved.

Figure 8:
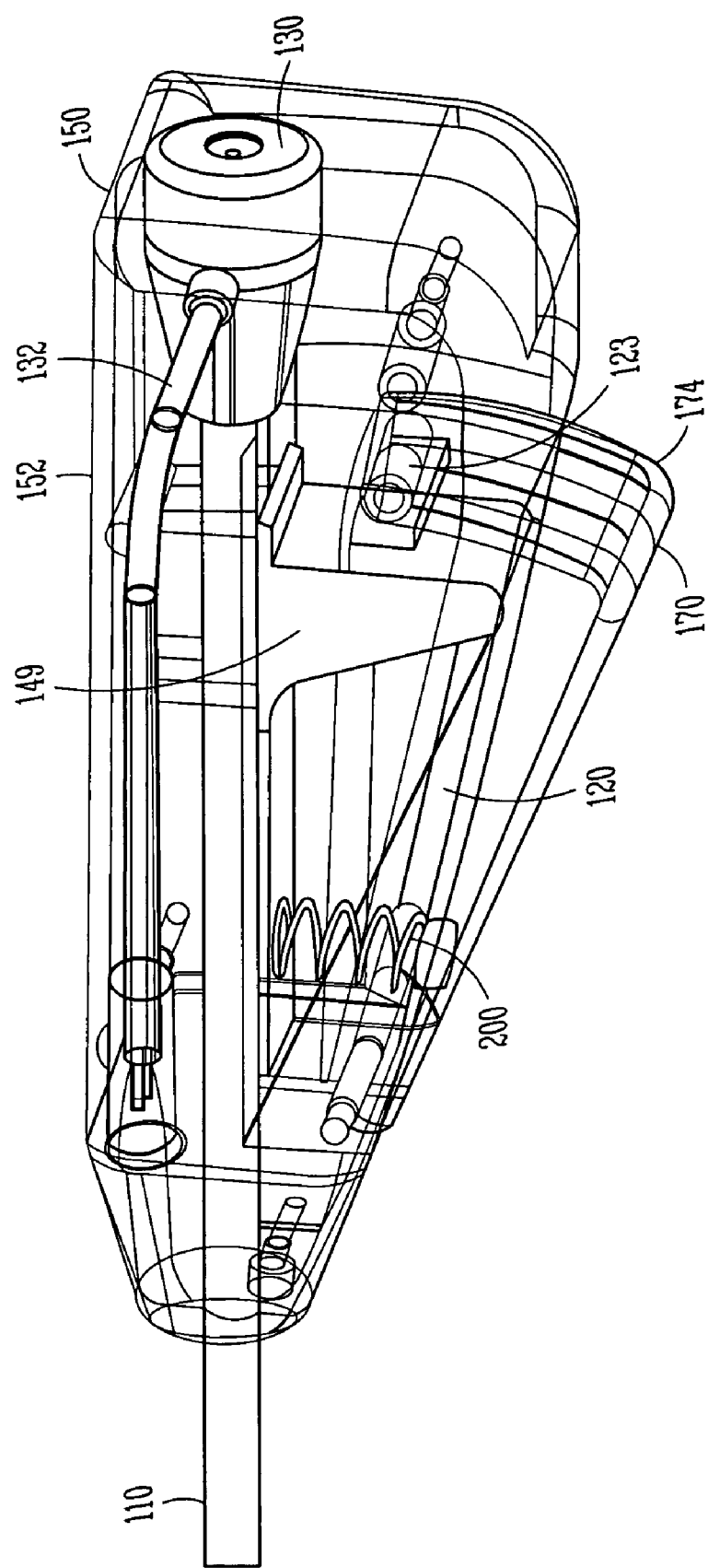
FIG. 8 illustrates a perspective view of a catheter assembly as constructed in accordance with at least one embodiment.

FIG. 8 illustrates another option for the internal mechanism. The pull wire 120 extends through the housing 152 and is anchored to anchor 123. The pull wire 120 is anchored, in one example, at its distal end to the anchor 123. The anchor 123 is mechanically fixed, in one option, to the actuator member 174, where movement of the actuator member 174, for example around the fulcrum, moves the anchor 123 and the pull wire 120.

The handle housing 152 includes a projection 149 extending from an internal portion of the housing 152. The projection 149 obstructs the path of the pull wire 120 when the pull wire 120 and/or anchor 123 are moved relative to the projection 149. For example, the actuator member 174 is moved from a first position to a second position, and the anchor 123 is moved therewith. The anchor movement moves the pull wire 120 and extends it over the projection 149, increasing the amount of pull wire 120 disposed within the handle housing 152, and decreasing the amount of pull wire 120 in the catheter body. This causes tension in the pull wire 120 and causes the distal end of the catheter body to deflect. When the lever actuator member 174 is released, the tension in the pull wire 120 is released, and the deflection in the distal end is released. It should be noted that the projection 149 and anchor 123 are one example of an internal mechanism where the length of the pull wire 120 is displaced, however, other variations are possible. For example, the projection 149 can be disposed on the lever actuator member 174, and the anchor can be disposed on the housing 152. In another option, the projection 149 could have a pulley or roller so the pullwire is not dragged across its surface.

Figure 9:
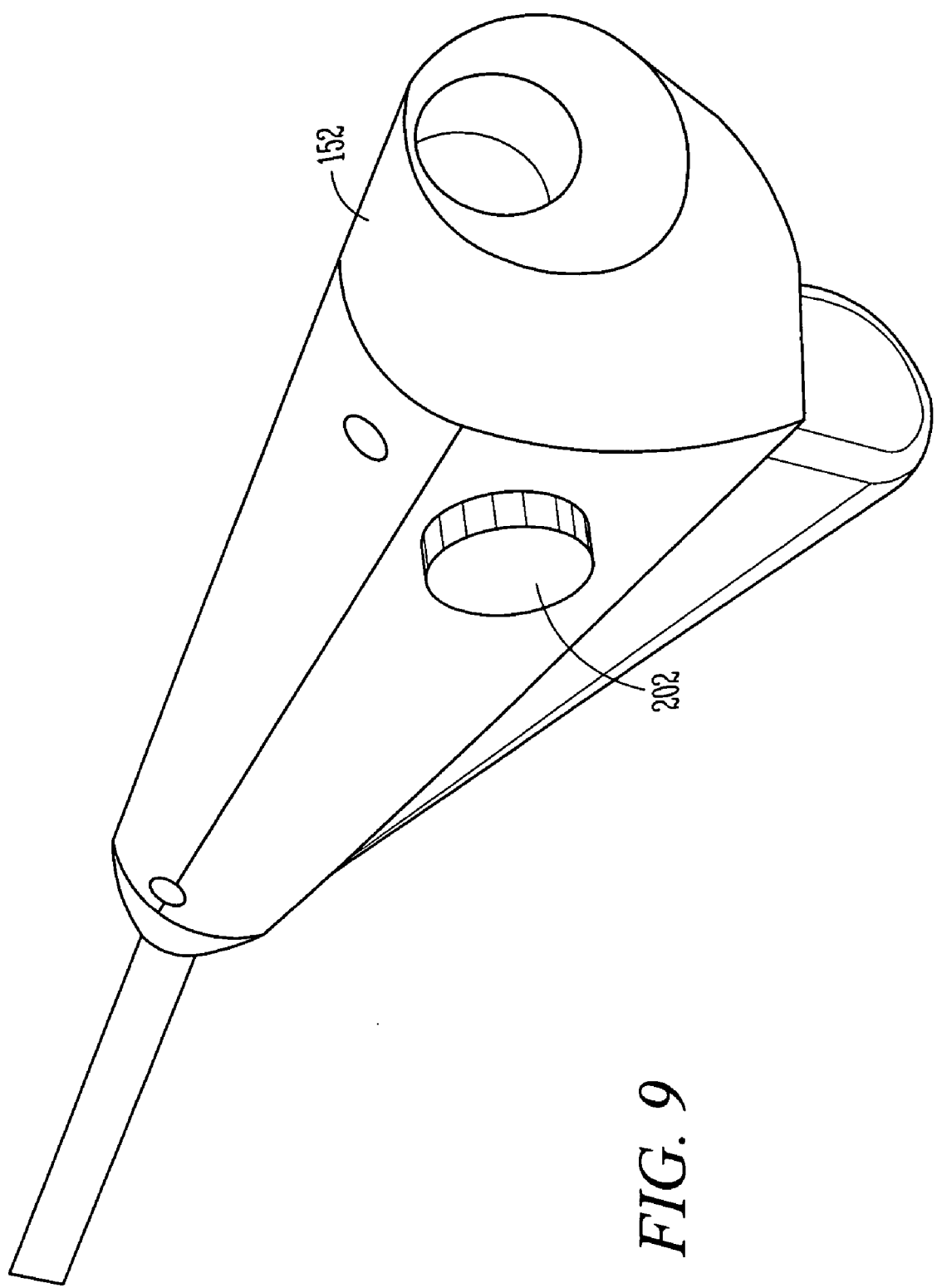
FIG. 9 illustrates a perspective view of a portion of a catheter assembly as constructed in accordance with at least one embodiment.
Figure 10:
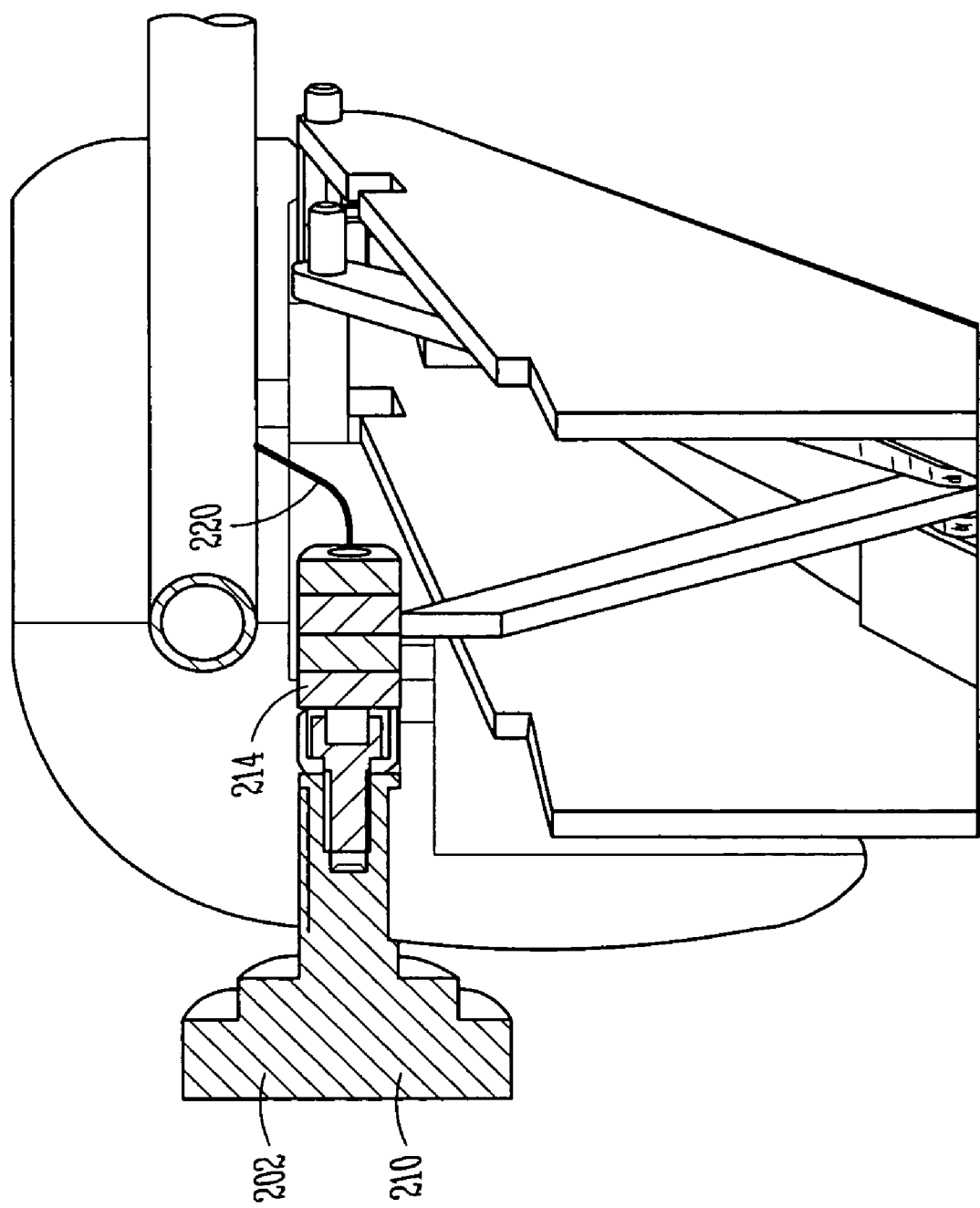
FIG. 10 illustrates a cut-away view of a portion of a catheter assembly as constructed in accordance with at least one embodiment.
Figure 11:
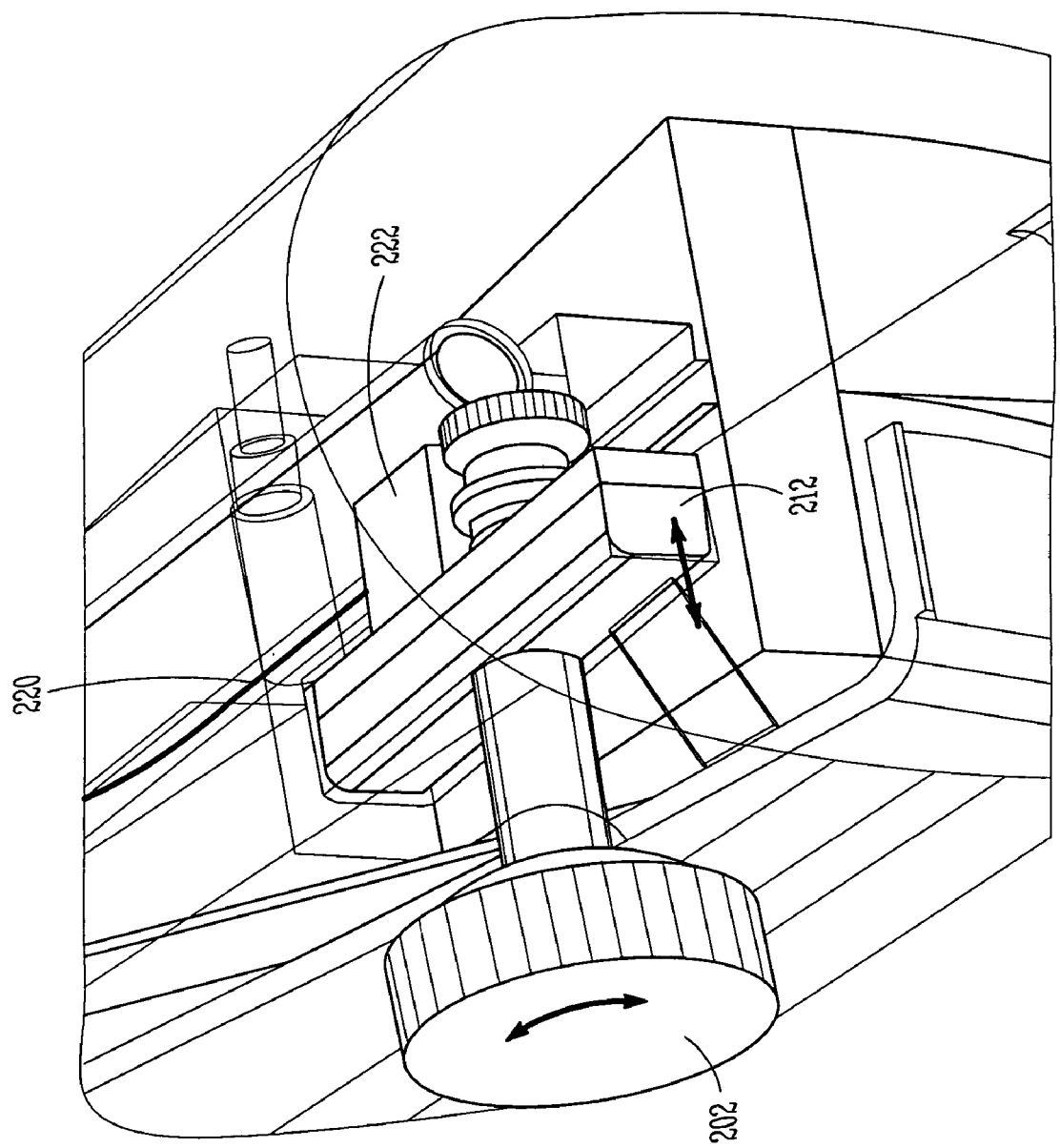
FIG. 11 illustrates a view of a portion of a catheter assembly as constructed in accordance with at least one embodiment.

In another option, the handle assembly 150 further includes a locking mechanism 202 associated therewith, as illustrated in FIGS. 9-11, or a locking mechanism 202 associated with the pull wire 220. It should be noted that the locking mechanism 202 or portions thereof can be incorporated with one or more of the various embodiments discussed above and below. In one option, the locking mechanism 202 is associated with the flexible element to lock the flexible element 220 in an intermediate position. One example of the locking is a mechanism that allows a user to place friction or pressure on the internal mechanisms described above, for example, the pull wire assembly. For example, a button or lever disposed along the handle assembly that operably prevents the one or more of the members of the internal mechanisms from moving.

One example is illustrated in FIGS. 9-11. For instance, a member, such as knob 210 is received at least partially within the housing 152. The knob 210 is rotatably coupled with a housing, for example through a threaded connection. A portion of the knob, for example, a distal portion 212, presses the pull wire assembly against a surface within the housing 152, and prevents movement of the pull wire 220 relative to the housing 152. For instance, the portion of the knob presses the pullwire assembly 222 against a surface on an opposite side of the pull wire assembly. It should be noted that other types of locking mechanisms can be used as well. For example, a locking mechanism which prevents movement of the pull wire relative to the housing.

The portion 212 can have a larger cross-sectional area than the rotatable part of the knob such that additional frictional forces can be placed on the pull wire assembly. The rotation of the knob 210 causes the portion 212 to move relative to the pull wire 220, however, the portion 212 may or may not rotate when the knob is rotated. In another option, a high friction member 214 is disposed along portion 212, providing additional frictional forces to the pullwire assembly 222.

In another embodiment, a method comprises manipulating a catheter assembly, the catheter assembly including a handle assembly, a catheter body controllable by a flexible element coupled with the handle assembly. An actuator member is coupled with the flexible element, where movement of the lever actuator member provides for movement of the flexible element and deflection of the distal end. The method includes moving the lever actuator member from a first actuator position to a second actuator position. The method further optionally includes moving the lever actuator member from a position along a first surface of the handle assembly toward a second opposite surface of the handle assembly, where moving the lever actuator member from the first actuator position deflects the distal end portion of the catheter body.

As the lever actuator is moved or manipulated, for example, with one hand, the internal mechanisms are manipulated, as discussed above. For example, internal linkages are manipulated, for example, by rotation. Alternatively, the pull wire length is displaced within the housing by a projection. It should be noted that a combination of these examples are also possible. Further options include locking the flexible element from movement, for example, relative to the housing.

Advantageously, the above-described deflectable catheter allows for increased control of the distal deflectable catheter end. The catheter allows for single-handed use of the device, and allows for a grip force to be exerted on the handle assembly. A large force can be produced by the user with grip force, and the device is useful for use with larger catheter shafts or thick-walled catheter shafts which are otherwise difficult to manipulate, or require a complicated mechanism to multiply force of the user.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A catheter assembly comprising:
   a handle assembly;
   a catheter body coupled with the handle assembly, the catheter body extending to a deflectable distal end portion, the deflectable distal end portion controllable by a flexible element;
   a lever actuator member operatively coupled with the flexible element, the lever actuator member having a first lever position and a second lever position, and movement of the lever actuator member provides for movement of the flexible element and the deflectable distal end portion
   a two bar linkage including a first bar rotatably coupled with a second bar at a rotatable joint, the first bar is rotatably coupled with the handle assembly and the second bar is attached to the flexible element, and the lever actuator member is separate from the two bar linkage and the lever actuator member is movably engaged with the two bar linkage at the rotatable joint, wherein the rotatable joint is movable along a portion of the lever actuator member; and
   the lever actuator member disposed along a first surface of the handle assembly, the lever actuator member deflectable toward a second surface when moving from the first position to the second position, where the first surface is opposite the second surface.

2. The catheter assembly as recited in claim 1, wherein the lever actuator member is movable into and out of an opening of the handle assembly.

3. The catheter assembly as recited in claim 1, wherein the lever actuator member is movable within a first plane, and the deflectable distal end portion is movable within a second plane, and the first plane is substantially non-parallel with the second plane.

4. The catheter assembly as recited in claim 1, wherein the catheter body includes a catheter body lumen therein, the handle assembly having a handle lumen therein, the catheter body lumen communicatively coupled with the handle lumen.

5. The catheter assembly as recited in claim 1, further comprising a spring coupled with the lever actuator member, where the spring facilitates movement of the actuator between the second position and the first position.

6. The catheter assembly as recited in claim 1, further comprising a lock member associated with the flexible element.

7. The catheter assembly as recited in claim 1, wherein the lever actuator member is a pivoting lever actuator member.

8. The catheter assembly as recited in claim 7, wherein the lever actuator member extends along greater than at least half a length of a handle length and the lever actuator member is operatively coupled with the handle assembly at a fulcrum.

9. The catheter assembly as recited in claim 1, wherein the first and second bars are rotatable about pivot points within the handle assembly as the lever actuator member is moved from the first position to the second position.

10. The catheter assembly as recited in claim 1, further comprising one or more roller assemblies associated with the two bar linkage at the rotatable joint, the one or more roller assemblies providing rolling engagement between the rotatable joint and the portion of the lever actuator member.

11. The catheter assembly as recited in claim 1, further comprising a pull wire displacement member disposed within the handle assembly.

12. A catheter assembly comprising:
a handle assembly;
a catheter body coupled with the handle assembly, the catheter body extending to a deflectable distal end portion, the deflectable distal end portion controllable by a flexible element, the deflectable distal end portion moveable from a distal portion first position to a distal portion second position;
a lever actuator member operatively coupled with the flexible element, the lever actuator member movable from a first lever position to a second lever position within a first plane, and movement of the lever actuator member provides for movement of the deflectable distal end portion within a second plane;
a two bar linkage, separate from the lever actuator member, including a first bar rotatably coupled with a second bar at a rotatable joint, the first bar is rotatably coupled with the handle assembly and the second bar is attached to the flexible element, and the lever actuator member is movably engaged with the two bar linkage at the rotatable joint, wherein the rotatable joint is movable along a portion of the lever actuator member; and
the first plane is substantially non-parallel with the second plane.

13. The catheter assembly as recited in claim 12, wherein movement of the lever actuator member provides for movement of the lever actuator member toward an interior portion of the handle assembly.

14. The catheter assembly as recited in claim 12, further comprising at least one resilient member operatively associated with the lever actuator member.

15. The catheter assembly as recited in claim 12, further comprising a locking mechanism associated with the flexible element, the locking mechanism preventing movement of the flexible element.

16. The catheter assembly as recited in claim 12, further comprising one or more roller assemblies operatively coupled with the two bar linkage at the rotatable joint.

17. The catheter assembly as recited in claim 16, wherein the one or more roller assemblies includes at least one handle roller and at least one actuator roller.

18. The catheter assembly as recited in claim 12, further comprising a pull wire projection and a pull wire anchor disposed within the handle assembly, and the flexible element extends laterally around the pull wire projection relative to the pull wire anchor and a longitudinal axis of the catheter body at the handle assembly.

19. A method comprising:
manipulating a catheter assembly, the catheter assembly including a handle assembly, a catheter body coupled with the handle assembly, the catheter body extending to a deflectable distal end portion, the deflectable distal end portion controllable by a flexible element and a lever actuator member, a two bar linkage including a first bar rotatably coupled with a second bar at a rotatable joint, the first bar is rotatably coupled with the handle assembly and the second bar is attached to the flexible element, and the lever actuator member is separate from the two bar linkage and the lever actuator member is movably engaged with the two bar linkage at the rotatable joint, wherein the rotatable joint is movable along a portion of the lever actuator member, and movement of the lever actuator member provides for movement of the flexible element;
moving the lever actuator member from a first actuator position to a second actuator position including moving the lever actuator member from a position along a first surface of the handle assembly toward a second opposite surface of the handle assembly; and
moving the lever actuator member from the first actuator position deflects the distal end portion of the catheter body.

20. The method as recited in claim 19, further comprising moving the lever actuator member along a first plane and moving the deflectable distal portion along a second plane, and the first plane is non-parallel with the second plane.

21. The method as recited in claim 19, wherein moving the lever actuator member includes moving the two bar linkage within the handle assembly.

22. The method as recited in claim 21, wherein moving the two bar linkage within the handle assembly includes rotating the first and second bars around first and second pivot points within the handle assembly.

23. The method as recited in claim 19, further comprising displacing the flexible element over a pull wire projection, and the flexible element extends laterally around the pull wire projection relative to the pull wire anchor and a longitudinal axis of the catheter body at the handle assembly.

24. The method as recited in claim 21, wherein deflecting the lever actuator member includes moving a pull wire anchor, where the pull wire anchor is fixed with the lever actuator member.

25. The method as recited in claim 19, further comprising locking movement of the flexible element.

26. The catheter assembly of claim 1, wherein the rotatable joint is movably engaged along a lever actuator member surface by a roller.

27. The catheter assembly of claim 12, wherein the rotatable joint is movably engaged along a lever actuator member surface by a roller.

28. The method as recited in claim 19, wherein moving the lever actuator member between the first actuator position and the second actuator position includes rolling the rotatable joint along a lever actuator member surface.

29. The catheter assembly of claim 1, wherein the lever actuator member is configured to receive a grip force, and the lever actuator member extends through only the first surface when moving from the first to the second position.

30. The catheter assembly of claim 12, wherein the lever actuator member is configured to receive a grip force, and the lever actuator member extends through the first surface and not the second surface when moving from the first to the second position.

31. The method as recited in claim 19, wherein moving the lever actuator member includes using a grip force to engage a first portion of the lever actuator member and forcibly position a second opposed portion of the lever actuator member inside the housing assembly, including moving the lever actuator member from a position along a first surface of the handle assembly toward a second opposite surface of the handle assembly.

* * * * *